United States Patent
Conrad-Vlasak et al.

(10) Patent No.: US 6,463,323 B1
(45) Date of Patent: Oct. 8, 2002

(54) ELECTRICALLY MEDIATED ANGIOGENESIS

(75) Inventors: Deena Conrad-Vlasak, Eden Prairie; Terence Pertile, Blaine; J. Edward Shapland, Shoreview; John Vanden Hoek, Elk River; Robert Walsh, Lakeville, all of MN (US)

(73) Assignee: EM Vascular, Inc., Shoreview, MN (US)

( * ) Notice: Subject to any disclaimer, the term of this patent is extended or adjusted under 35 U.S.C. 154(b) by 0 days.

(21) Appl. No.: 09/743,836
(22) PCT Filed: Nov. 12, 1999
(86) PCT No.: PCT/US99/26834
§ 371 (c)(1), (2), (4) Date: May 21, 2001
(87) PCT Pub. No.: WO00/27466
PCT Pub. Date: May 18, 2000

Related U.S. Application Data
(60) Provisional application No. 60/108,080, filed on Nov. 12, 1998.

(51) Int. Cl.$^7$ ............................................... A61N 1/00
(52) U.S. Cl. .......................................................... 607/2
(58) Field of Search ............................ 600/9–15; 607/1, 607/2

(56) References Cited

U.S. PATENT DOCUMENTS 3,745,995    7/1973    Kraus ........................ 128/82.1

(List continued on next page.)

FOREIGN PATENT DOCUMENTS

| WO | WO 97/25098 | 7/1997 | ............ A61N/1/00 |
| WO | WO 98/10830 | 3/1998 | ............ A61N/1/362 |
| WO | WO 99/03533 | 1/1999 | ............ A61N/1/362 |

OTHER PUBLICATIONS

Spinale, Francis G., et al. entitled "Mycocardial matrix degradation and metalloproteinase activation in the failing heart: a potential therapeutic target" from Cardiovascular Research, vol. 46, #2, May 2000, pp. 225–238.

Kanno, Shinichi, et al., entitled "Establishment of a Simple and Practical Procedure Applicable to Therapeutic Angiogenesis" from Circulation 1999; 99: 2682–2687.

*Primary Examiner*—Scott M. Getzow
(74) *Attorney, Agent, or Firm*—Nikolai & Mersereau, P.A.; Thomas J. Nikolai

(57) ABSTRACT

This invention is an electrical stimulation apparatus for delivering an electrical field over a predetermined period of time to a targeted body tissue in order to stimulate a cell initiated angiogenic response in living cells within the targeted body tissue. The electrical stimulation apparatus includes an electrical field generating unit including a power support, a control mechanism interconnected with the power supply, and a plurality of electrodes designed to generate an electrical field proximate to the targeted body tissue. The amplitude of the electrical field delivered to or generated proximate to the targeted body tissue, and the duration of the period of delivery is sufficient to stimulate angiogenesis in the targeted body tissue. The control mechanism preferably includes a computer unit in electronic communication with the power supply, the computer being programmed to cause the electrical stimulation apparatus to deliver a predetermined amount of electrical current or voltage over a predetermined period of delivery to the plurality of electrodes such that the electrical stimulation apparatus can deliver such electrical current or voltage to the targeted body tissue when the plurality of electrodes are in contact or proximity with the targeted body tissue.

30 Claims, 11 Drawing Sheets

U.S. PATENT DOCUMENTS

| | | | |
|---|---|---|---|
| 3,890,953 | 6/1975 | Kraus et al. ................. 128/1.5 |
| 3,915,151 | 10/1975 | Kraus ........................ 128/1.5 |
| 4,266,532 | 5/1981 | Ryaby et al. ................ 128/1.5 |
| 5,334,222 | 8/1994 | Salo et al. .................... 607/17 |
| 5,401,233 | 3/1995 | Erickson et al. ............. 600/14 |
| 5,433,735 | 7/1995 | Zanakis et al. .............. 607/50 |
| 5,450,859 | 9/1995 | Litovitz ...................... 128/897 |
| 5,544,665 | 8/1996 | Litovitz et al. ............. 128/897 |
| 5,566,685 | 10/1996 | Litovitz et al. ............. 128/898 |
| 5,634,899 | 6/1997 | Shapland et al. ............. 604/51 |
| 5,800,528 | 9/1998 | Lederman et al. ............. 623/3 |
| 5,855,570 | 1/1999 | Scherson et al. ........... 604/304 |
| 5,968,527 | 10/1999 | Litovitz ..................... 424/400 |
| 6,200,259 | 3/2001 | March .......................... 600/9 |

ELECTRICALLY MEDIATED ANGIOGENESIS

REFERENCE TO CO-PENDING U.S. APPLICATIONS

This application claims priority to U.S. patent applications entitled, ELECTRICALLY MEDIATED ANGIOGENESIS, filed Nov. 12, 1998, as application Ser. No. 60/108,080; MULTI-LEAD SENSING AND LOCAL DRUG DELIVERY TO THE HEART MUSCLE, filed Nov. 12, 1998, as application Ser. No. 09/190,412; and APPARATUS AND METHOD FOR EMPLOYING ELECTRICAL ENERGY TO ENHANCE ADMINISTRATION OF AN AGENT, filed Nov. 12, 1998, as application Ser. No. 09/191,209; the disclosures of which are hereby incorporated herein by reference.

TECHNICAL FIELD

The present application relates to angiogenesis, and more particularly to the electrically mediated upregulation of angiogenic factors to promote revascularization of ischemic body tissue.

BACKGROUND

Current medical practices call for diagnosing, testing and treating certain maladies and injuries with various agents. In the past few years there have been great strides in the development of agents that have improved therapeutic and diagnostic application. For example, scientists and medical researchers are rapidly developing genetic materials and other agents that cause cells to participate in the generation of new blood vessels; a process called angiogenesis. There are believed to be two main types of vascular disease which are especially suitable for treatment by angiogenesis therapy, namely coronary artery disease and peripheral vascular disease.

Coronary artery disease is a disease that restricts the flow of blood to the myocardial tissue of the heart. This restricted blood flow is commonly caused by a blockage or blockages resulting from a disease process known as arteriosclerosis. The blockages can cause an infarction where the flow of blood to a certain part of the myocardium or cardiac muscle is interrupted, generally resulting in a localized area of dead myocardial tissue that is surrounded by an area of myocardial tissue receiving reduced blood flow. This area of reduced blood flow is called a zone of ischemia. Other people suffer from diffuse coronary disease, which is the blockage of many coronary arteries. By-passing or reopening all of these arteries is not an option because of the extreme procedural difficulties and trauma that such a procedure would cause. As a result, there exists a need to provide an adequate flow of blood to ischemic areas of the heart without resorting to by-pass surgery or efforts to reopen the blocked vessels. Ischemia in the heart is generally present in those with coronary vessel blockage which results in a heart attack.

Peripheral vascular disease is indicated when blood flow is restricted to areas other than the myocardium. These ischemic areas are often induced by vascular blood clots or degenerative diseases. One example is the ischemic limb. The ischemic limb often occurs in patients having diseases such as diabetes. In a diabetic patient, the small vessels are often destroyed causing certain tissue areas to be oxygen and nutrient deficient, or ischemic. Areas of ischemic tissue also result from strokes. In the case of a stroke, the cerebral blood flow is impaired due to a thrombosis, hemorrhage or embolism.

One way to address the need for improved blood flow to ischemic tissues in the body is to treat such tissues in such a way that the tissue or tissues generate new blood vessels. As stated above, the process of creating or generating new blood vessels is called angiogenesis. One method to promote angiogenesis is by direct injection of an angiogenic agent. One technique for delivery of such an agent to an ischemic area involves the direct injection of genetic material in or near the ischemic area to promote angiogenesis.

In practice, however, direct injection also has many shortcomings. One shortcoming is the inefficiency in transferring the genetic material into the cells and relatively low level of stable transfection of the genetic material within target cells. The transfection efficiency of such local such delivery by direct injection is generally believed to be about 1% to 2%.

Another method of direct injection employs electroporation, or a treatment of tissue with a series of high-energy electrical pulses to porate the tissue and allow the genetic material to enter. One problem with this approach is that many healthy cells are frequently killed in the process and overall transfection is still not very high.

The inability to effectively deliver the angiogenic agent to the targeted area, therefore is one of the major limitations of the use of such agents. During delivery of such agents, large amounts are often destroyed or lost to general circulation. This is inefficient, expensive, and can promote toxicity in certain regions. Other side effects are also possible in healthy tissue due to the inefficiency of such local delivery methods.

Therefore, there is a need for improved methods for enhancing angiogenesis and the cellular expression of agents to promote angiogenesis. There is also a need for a treatment apparatus that is cost effective and reduces the risk of side effects. There is also a need for a method and/or device that utilizes the body's natural healing mechanisms to promote angiogenesis, while avoiding the need for any introduction of foreign agents.

SUMMARY OF THE INVENTION

The present invention provides an electrical stimulation apparatus for delivering an electrical field to a targeted body tissue over a predetermined period of time in order to stimulate a cell-initiated angiogenic response in living cells within the targeted body tissue. The electrical stimulation apparatus having an electrical field generating unit including a power supply and a control mechanism interconnected with the power supply; and a plurality of electrodes designed to deliver an electrical field to the targeted body tissue. The plurality of electrodes are in electrical communication with the power supply and the control mechanism controls an amplitude and a duration of a period of delivery of electrical pulse from the power supply to the respective electrodes and through the targeted body tissue when the electrodes are in contact with the targeted body tissue at a plurality of first locations. The amplitude of the electrical field delivered to the targeted body tissue and the duration of the period of delivery is sufficient to stimulate angiogenesis in the targeted body tissue; preferably by causing living cells within the targeted body tissue to increase vascular endothelial growth factor (VEGF) expression.

In one embodiment of the present invention, the electrical field generating unit is a constant current delivery device and the electrical field is generated by the constant current delivery device. The amplitude of the electrical current delivered to the targeted body tissue by the constant current delivery device is preferably from about 01. mA to about 250 mA and the duration of the period of delivery is preferably equal to or greater than about 1 ms.

In another embodiment of the present invention, the electrical field generating unit is a constant voltage delivery device and the electrical field is generated by the constant voltage delivery device. The amplitude of the electrical voltage delivered to the targeted body tissue by the constant voltage delivery device is preferably a generally constant voltage of from about 50V/cm to about 300V/cm. In further preferred embodiments, the electrical field is produced by a number of pulses in the range of from 1 to about 1000 pulses with a frequency between about 0. 1 Hz to about 5 Hz and the electrical field is preferably generated for a duration between about 0.0001 seconds to several days.

In other preferred embodiments, the control mechanism includes a computer processing unit in electronic communication with the power supply, the computer processing unit being programmed to cause the electrical stimulation apparatus to deliver a predetermined amount of electrical current or voltage over a predetermined period of delivery to the plurality of electrodes such that the electrical stimulation apparatus can deliver such electrical current or voltage to the targeted body tissue when the plurality of electrodes are in contact or in proximity with the targeted body tissue. In other preferred embodiments, the plurality of electrodes are configured in a manner selected from the group consisting of unipolar, bipolar, and multiple electrode configurations and the apparatus is preferably designed and configured to be implantable.

The present invention also includes a method of treatment of targeted body tissues by: (1) providing living cells, preferably autologous or heterologous living cells, more preferably autologous or heterologous myocardial cells for treatment of myocardial tissue, which, in the case of autologous cells, have been removed from the prospective patient, which are biologically compatible with the targeted body tissue; (2) stimulating the living cells with an electrical field sufficient in a manner describe herein to increase VEGF expression by the living cells, wherein the amplitude of the electrical field delivered to the targeted body tissue and the duration of the period of delivery is sufficient to cause the living to increase VEGF expression; and (3) injecting the stimulated cells into the targeted body tissue.

The present invention has several advantages. For example, angiogenesis can be promoted without the delivery of foreign agents, which allows the body to heal naturally and minimizes potential for side effects. The procedure provides minimum discomfort and may be performed on an outpatient basis. The main power supply can be reused, while the electrodes are disposable. A combination of a reusable power supply and disposable sterilized electrodes reduces both the expense and the chance of contamination. Yet another advantage is that electrical energy can be applied for extended periods of time with minimal risk of killing the target cells.

Another advantage is that the present invention can be used to treat deep tissues, as well as superficial tissue. Certain techniques may be either invasive, minimally invasive, or noninvasive. Furthermore, the treatment of the ischemic tissue can be targeted while exposure to healthy tissue is minimized.

The above described features and advantages along with various other advantages and features of novelty are pointed out with various other advantages and features of novelty are pointed out with particularity in the claims of the present application. However, for a better understanding of the invention, its advantages, and objects attained by its use, reference should be made to the drawings which form a further part hereof and to the accompanying descriptive matter in which there is illustrated and described preferred embodiments of the invention.

DETAILED DESCRIPTION OF THE PREFERRED EMBODIMENTS

Figure 1A:
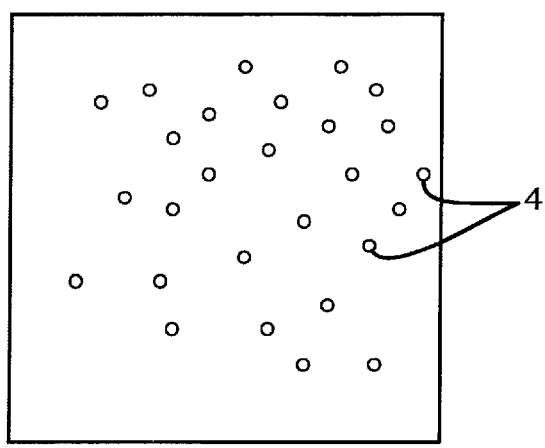
FIGS. 1A–1C, taken in series. diagrammatically illustrate initial in vitro capillary formation overtime between untreated free cells and free cells induced in accordance with a preferred embodiment of the present invention.

Various embodiments of the present invention are described below in detail with reference to the drawings, wherein like reference numerals represent like parts and assemblies throughout the several views. Reference to the various embodiments is not intended to limit the scope of the invention.

In general, the present invention relates to an apparatus for generating an electrical field proximate to or within a targeted body tissue and methods of treatment of such targeted body tissues with such an apparatus to stimulate an angiogenic response within living cells in such body tissues. In these methods, electrical energy is delivered directly to cells in the targeted body tissue which located in an electrical path between at least two electrodes of such an apparatus. Such delivery is believed to promote a cell-initiated angiogenic response that promotes angiogenesis in targeted body tissues which can include body tissues in ischemic zones. The cell-initiated angiogenic response is believed to include a cellular process of capillary formation which is initiated or accelerated following application of electrical stimulation of body tissues.

Figure 1B:
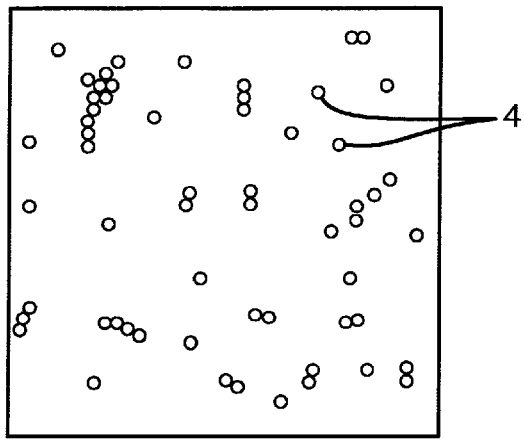
Figure 1C:
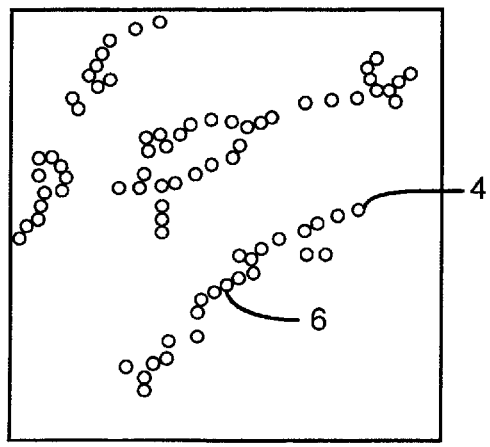

Referring now to the drawings, the cellular process of capillary formation during electrically-mediated angioenesis is illustrated in FIGS. 1A–1C. FIG. 1A illustrates an array of epithelial cells 4 in culture distributed in a normal growth pattern before the application of an electric current. FIG. 1B illustrates the beginning stages of angiogenesis following electrical stimulation in which the cells 4 begin to organize and align. FIG 1C illustrates what is believed to be the initial formation of the tube structures 6 in such cell culture. It is believed that these tube structures 6 are believed to develop into new capillaries. A discussion of the aggregation of these cells will follow below.

Figure 2A:
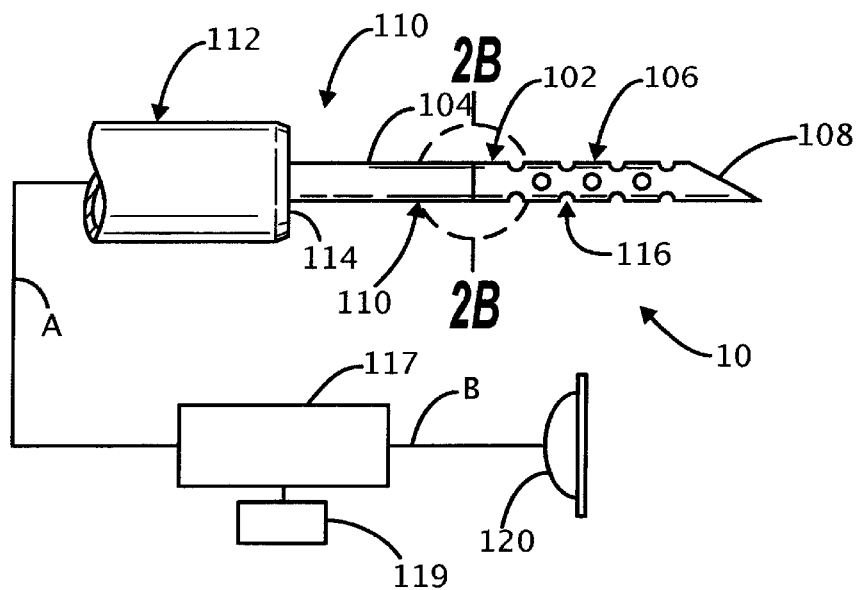
FIG. 2A schematically illustrates an electrical stimulation apparatus for generating an electrical field to enhance angiogenesis in ischemic, and other targeted body tissues.
Figure 2B:
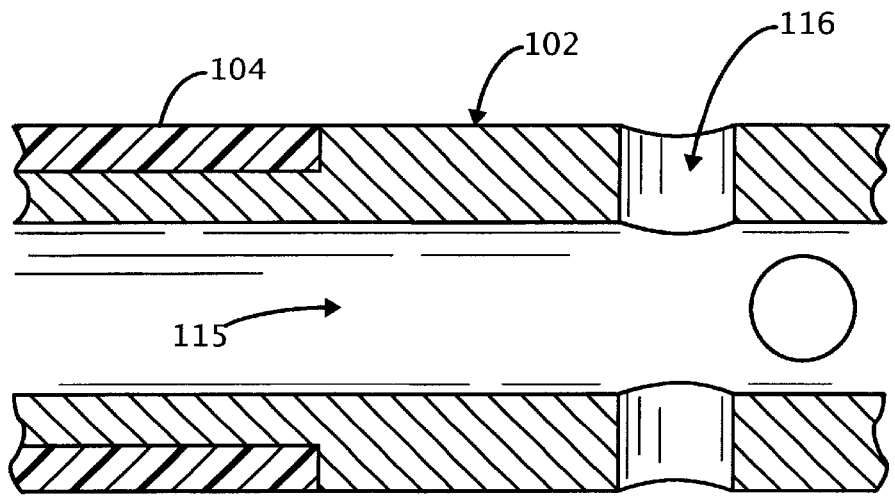
FIG. 2B is an enlarged broken away side view of a portion of electrical stimulation apparatus shown in circle 2B—2B of FIG. 2A.

FIGS. 2A and 2B schematically illustrate an electrical stimulation apparatus 10 of the present invention useful for stimulation of ischemic tissue and other targeted body tissues by the delivery of low amperage electric current. The apparatus 10 includes a needle 100 having a proximal portion 112 and a distal portion 110. The distal portion 110 includes an electrically conductive shaft 102 which forms a primary electrode, an insulating material 104 partially covering the shaft 102, a delivery zone 106, and a distal tip 108. The shaft 102 has a lumen 115 and a plurality of delivery ports 116. The diameter of the proximal portion 112 is greater than the diameter of the distal portion 110. A radially oriented surface 114 defines a distal end of the proximal portion 112 and forms a depth guide 114 that generally limits the distance that the proximal end 112 of the needle 100 can be inserted into the patient's body tissue. The distance between the distal tip 108 of the needle 100 and the depth guide 114 can vary depending on how deep the intended target area is from the surface of the body tissue into which the needle 100 is to be inserted.

Figure 3:
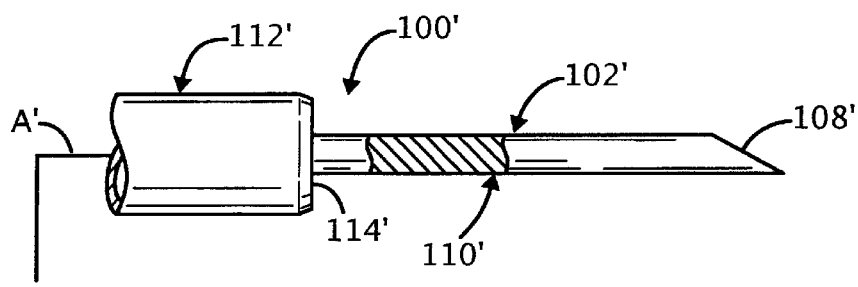
FIG. 3 schematically illustrates an alternative embodiment of the electrical stimulation apparatus shown in FIG. 2A.

The needle 100 also defines a lumen 115 and defines delivery ports 116 in the distal portion 110. The lumen 115 and delivery ports 116 enable injection of a liquid into the targeted body tissues, including agents such as an angiogenic agents and/or cooling mediums to minimize heating of the targeted body tissue. In alternative embodiments such as that illustrated in FIG. 3, the needle 100' is solid and does not include delivery ports, so that fluids cannot be injected through the distal portion of the needle 100'.

Figure 11A:
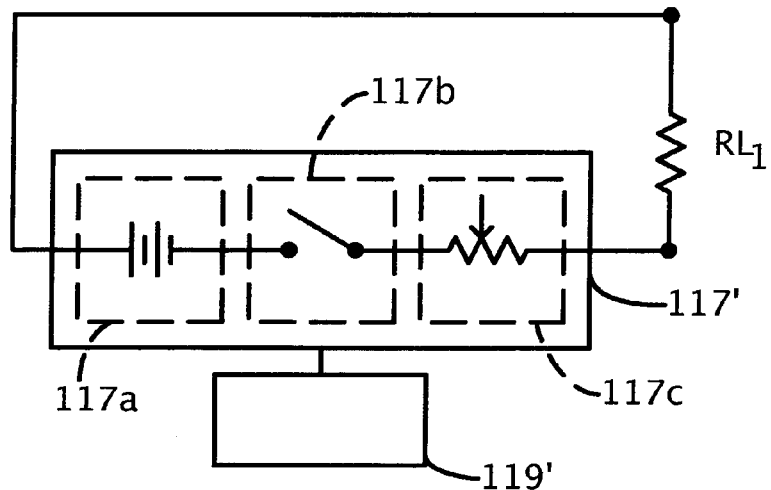
FIGS. 11A–11D schematically illustrate circuits which are representative of alternate circuits which can be employed when certain of the alternate electrical stimulation apparatti of the present invention are employed to deliver an electrical field to various targeted body tissues.
Figure 11B:
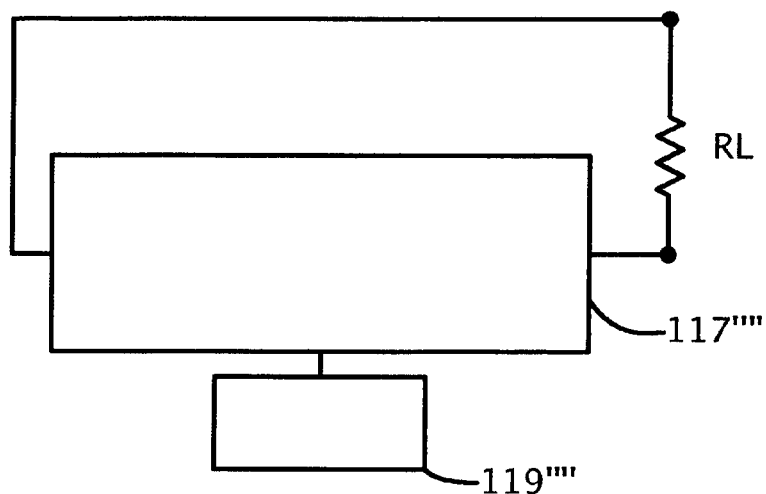
Figure 11C:
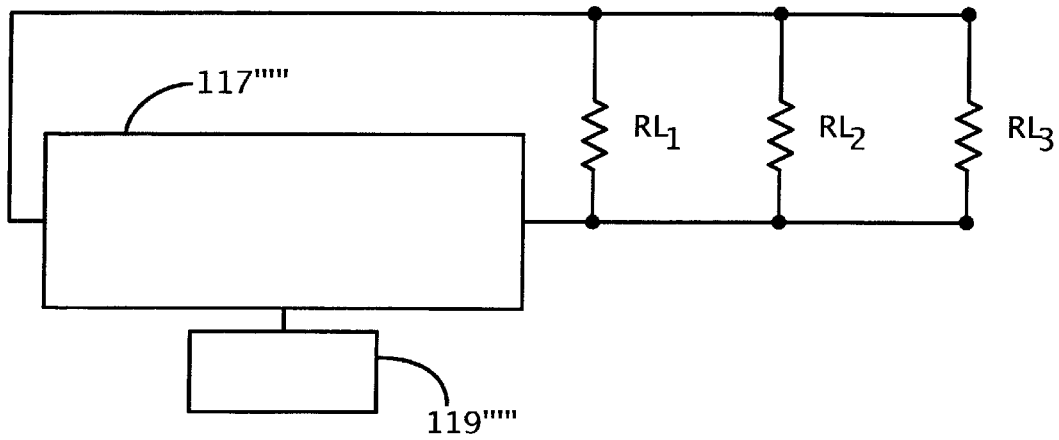

Referring now again to FIG. 2A, the needle 100 is in electrical communication via electrical lead A with an electrical field generating unit (EFGU) 117. The EFGU 117 is in electrical communication with a control mechanism 119. In preferred embodiments, the control mechanism 119 is a computer processing unit which is programmed to generate a preferred electrical field within a proximate to a targeted body tissue. In an alternate embodiment of the present invention shown in the circuit diagram in FIG. 11A, the EFGU 117' will include an electrical power supply 117a, a switch 117b and a variable resistor so that the current may be varied and the circuit can be broken. In other embodiments the EFGU 117 is a constant current delivery device, such as an iotophoretic electrical current generation device such as the constant current delivery device (CCDD) sold by EMPI, Inc. with a system sold under the tradename DUPEL®, or the CCDD sold by IOMED, Inc. which is DC powered "dose controller." In order to effectively provide computer controls for the CCDDs, appropriate modifications are made to provide for programmed control of these devices by a CPU 119'. If the EFGU 117 is a constant voltage delivery-device (CVDD), then a device similar to the PA-4000 sold by CYTOPULSE, Inc. will be used.

Referring again-to FIG. 2A, a flexible, patch-type electrode 120 is also in electrical communication with the source of current 117 via electrical lead B so that it has an opposite polarity from the delivery zone 106 of the needle 100. In alternative embodiments an additional needle can be used in place of the patch-type electrode 120 or, converesely, an additional patch-type electrode (hereinafter patch) can be used in place of the needle 100. The source of current 117 will generally include a signal generator, a variable resistor, a switch, or other circuitry that is electrically connected to the source of current 117 in certain embodiments in order to shape or otherwise control the signal used to pass electric current through the electrodes. In preferred embodiments, the source of current 117 is controlled by a microprocessor or other computer processing unit (CPU) 119 which is preferably programmed to cause the electrical stimulation apparatus to deliver a predetermined amount of electrical current over a predetermined period of delivery to the plurality of electrodes such that the electrical stimulation apparatus can deliver such electrical field to the body tissue when the plurality of electrodes are in contact with the body tissue. Electrodes of all types can be used, especially including those disclosed in U.S. patent application Ser. No. 08/898,410, filed Jul. 22, 1998 and entitled NEEDLE FOR IONTOPHORETIC DELIVERY OF AN AGENT, the disclosure of which is hereby incorporated herein by reference.

Alternative configurations of the electrical stimulation apparatus (not shown) also include multiple needles. In a further alternate embodiment, for example, there are two needles, two patches, or a needle and a patch having the same polarity and a further needle or. patch having the opposite polarity. In another possible configuration, there is an array of electrodes, possibly needles with at least one electrode, or needle having one polarity and at least one other electrode or needle, preferably a plurality, having an opposite polarity similar to that illustrated in the schematic circuit drawing shown in FIG. 11D where there are five electrodes of one polarity and a single electrode of opposite polarity. In yet another embodiment, illustrated in FIG. 10 and discussed below, there is a sensing electrode 138 separate from the positively and negatively charged electrodes 130 and 120, respectively, which is especially useful for cardiovascular applications. In this embodiment, the sensing electrode 138 is used to sense the electrical activity of the heart 128 and pace delivery of the electrical energy as disclosed in U.S. Pat. No. 5,634,899, issued Jun. 3, 1997, and entitled SIMULTANEOUS CARDIAC PACING AND LOCAL DRUG DELIVERY METHOD, the disclosure of which is hereby incorporated herein by reference. In this regard, it is noted that the heart muscle is in a state of general relaxation during a "refractory period" which follows each contraction of the heart muscle. in preferred embodiment, treatments of ischemic zones of the myocardium are synchronized so that pulses of electrical energy are generated to deliver an electrical field to the heart during these refractory periods in order to reduce the risk of creating an arrhythmia. In preferred embodiments, the apparatus will monitor the heart 128 with a sensing lead 136 so that the CPU 118 can provide the programmed synchronization necessary to provide the appropriate timing to deliver pulses during the refractory period In further embodiments, the sensing lead 136 in coordination with the CPU 118 will also have heart pacemaking capabilities to allow it to pace the heart 128 to facilitate the synchronization of the pulsed electrical field generation with the occurrence of the refractory period.

Figure 4A:
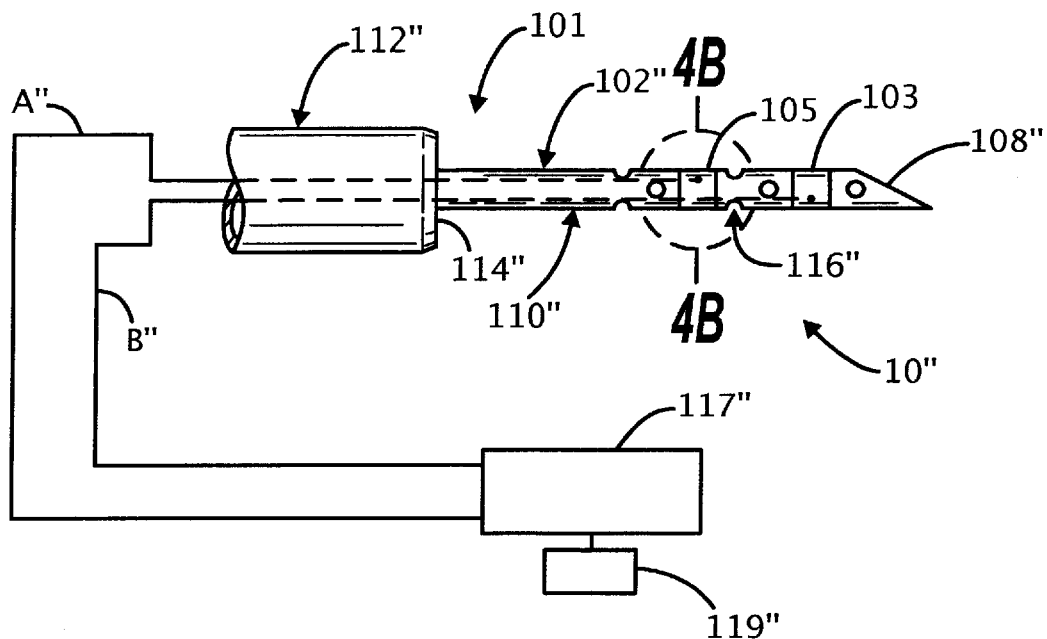
FIG. 4A illustrates an alternate electrical stimulation apparatus having a single needle having two electrodes having opposite polarity in a "bipolar" needle configuration.
Figure 4B:
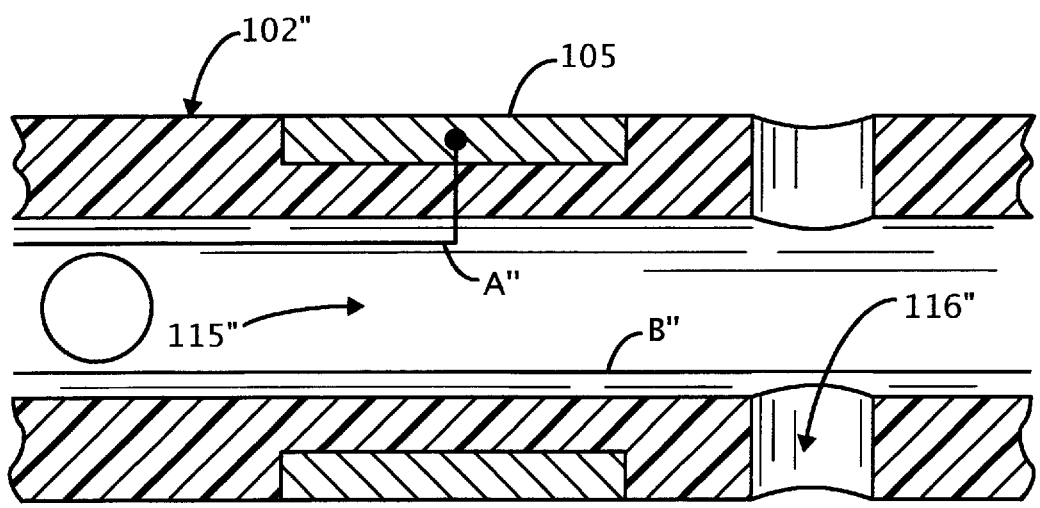
FIG. 4B is an enlarged broken away side view of a portion of the electrical stimulation apparatus shown in circle 4B—4B of FIG. 4A FIG. 5 schematically illustrates an alternative application of the apparatus shown in FIG. 2.

Another alternative embodiment of the electrical stimulation apparatus 10 shown in FIG. 2 is shown in FIGS. 4A–4B. In this embodiment the apparatus 10" includes a bipolar needle 101 having a proximal portion 112" and a distal portion 110". The proximal portion 112" has a depth guide 114" and the distal portion 110' has a shaft 102', an insulating material 104', a delivery zone 106', a distal tip 108', and a first electrode 103 that extends around the circumference of the needle 101. A second electrode 105 is spaced apart from the first electrode 103 and also extends around the circumference of the needle 101. In one possible embodiment, the needle 101 is formed from a nonconductive material, such as a ceramic material or hard polymer such a polycarbonate, high density polyethylene and the like, so that the first and second electrodes 103, 105 are electrically isolated from one another. In an alternative embodiment (not shown), a nonconductive material or substrate is positioned between the needle and the first and second electrodes. The electrodes and can be formed as described herein including coils wrapped around the needle, electrically conductive ink, and electrically conductive bands or foil.

Electrical leads B", A" provide electrical communication between the EFGU 117" and the first and second electrodes 103 and 105 such that the first electrode 103 has an opposite polarity from the second electrode 105. In this configuration, one of the electrodes is an anode and the other electrode is a cathode. An alternative configuration (not shown) includes multiple anodes and/or multiple cathodes mounted on a needle. Other alternative configurations include multiple needles. Furthermore, the polarity of the first and second electrodes 103 and 105 can be switched by programming the CPU 119" to switch the polarity of the respective electrodes when the EFGU 117" permits such switching.

Figure 5:
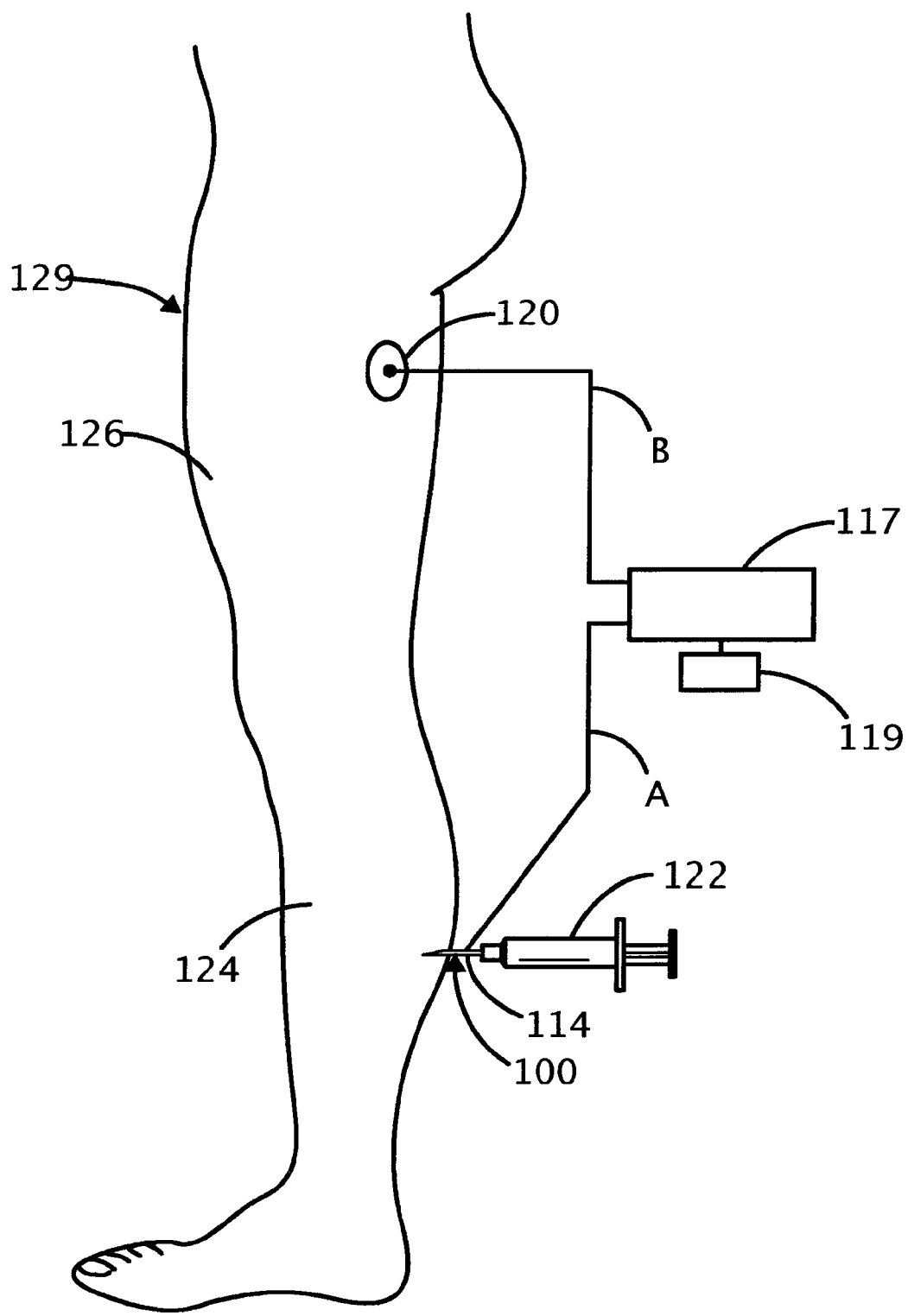

In one possible application as shown in FIG. 5, the needle 100 is attached to a syringe 122 for injection of an agent or a cooling liquid and is then inserted into or proximal a target area in a diseased limb, such as a lower leg 124, until the depth guide 114 is against the surface of the delivery area. The patch-type electrode 120 is attached to the surface of the patient's body 129 in a convenient location such as the thigh 126. Next, current delivery is initiated between the needle 100 and the patch-type electrode 120. A single or multiple insertions may be used. The bipolar needle 101 may also be used in a somewhat similar application. The primary difference when using the bipolar needle 101 is that there is no need to attach a patch-type electrode to the patient's skin.

Figure 6:
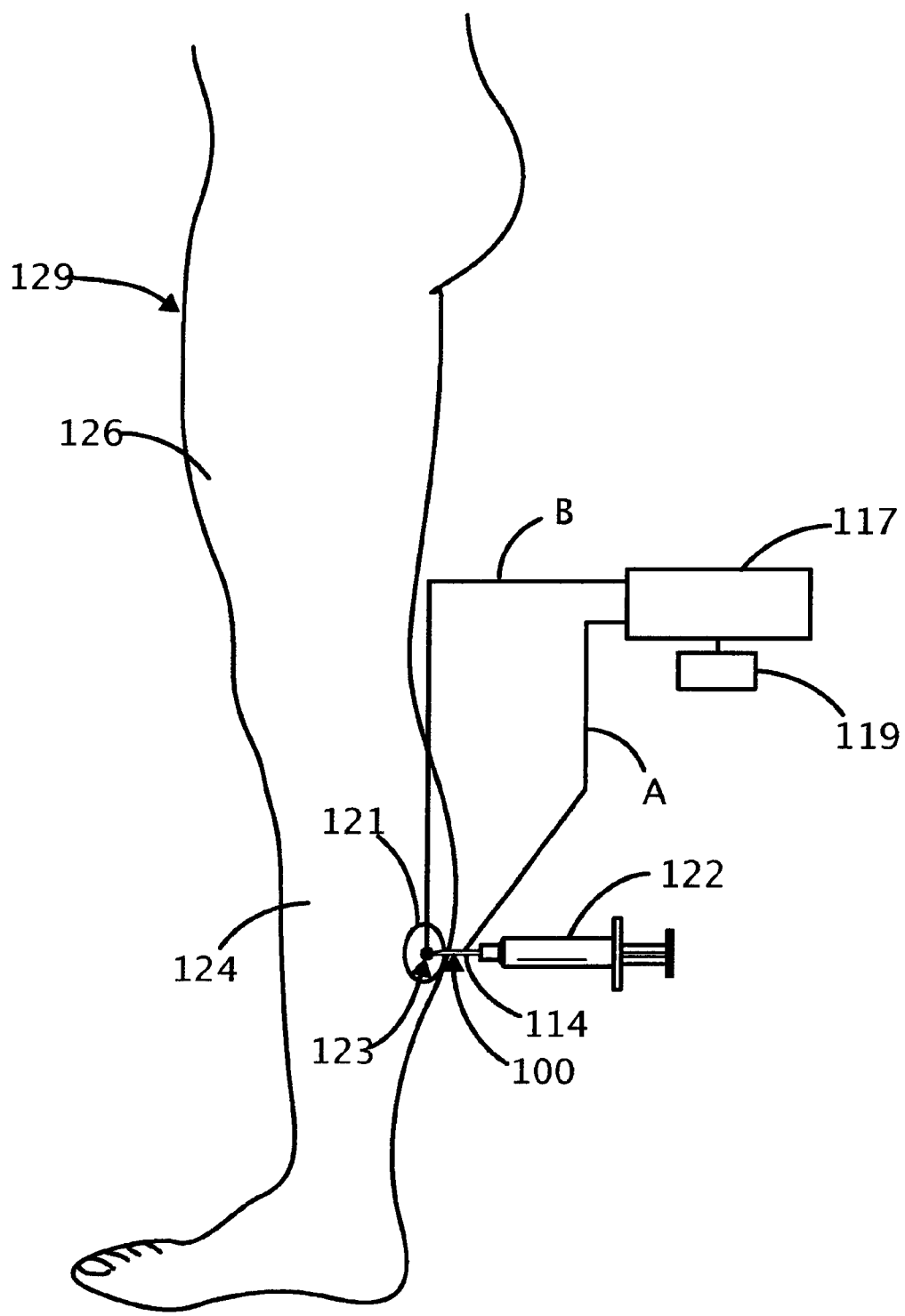
FIG. 6 schematically illustrates an alternative application of the electrical stimulation apparatus shown in FIG. 2.

In an alternative embodiment as shown in, FIG. 6, a patch-type electrode 121 defines an opening 123 that passes therethrough. The patch-type electrode 121 is positioned against the surface of the skin at a site that is adjacent or over the target area of tissue. The caregiver then inserts the needle 100 through the opening 123 and into the target area of tissue until the depth guide 114 is against the surface of the skin. In this position, the needle 100 is not in direct electrical contact with the electrically conductive portions of the patch-type electrode 121. Current is then generated between the needle 100 and the patch-type electrode 121.

The current in any of the alternate applications can have different waveforms including direct current, alternating current and pulsed. Any well-known waveforms can be used including those which are described in U.S. Pat. No. 5,499,971, which issued on Mar. 19, 1996 and is entitled INTERNAL IONTOPHORESIS DRUG DELIVERY APPARATUS AND METHOD, the disclosure of which is hereby incorporated herein by reference. In one possible embodiment, a low level of current between about 0.1 mA and about 50 mA, preferably between about 0.2 mA and about 25 mA, more preferably between about 0.4 mA and about 10 mA, and more preferably between about 0.5 and about 5 mA is preferably conducted between the electrodes. In one possible embodiment that uses direct current, the amplitude is between about 0.5 to 5 mA although other current amplitudes can be used.

In an embodiment that uses pulsed or alternating waveform, the amplitude of the current can be adjusted in relation to the pulse width and duty cycle, which allows control over the overall density of the current being emitted from the electrode. In one possible embodiment using pulsed or alternating waveforms, the amplitude of the signal is in the range from about 5 mA to about 250 mA, and the pulse width is in the range from about 0.1 ms to about 100 ms. In certain embodiments, the treatment may generating pulses having a current of 1 mA for a period of 1 minute in one or more, perhaps 5 of more, locations. Alternately, a 5 mA pulse can be delivered for 5 seconds in 5 second intervals for an extended period of 1 minute and repeated a one to five different locations. Alternately, 250 mA pulses can be delivered for 15 msec every second for one minute. In another preferred embodiment of the present invention, the preferred apparatus allows for the delivery of constant voltages generally in the range of from about 1 V/cm to about 500 V/cm (applied voltage divided by the distance in cm separating the respective electrodes); preferably from about 5 V/cm to about 250 V/cm, and more preferably from about 10 V/cm to about 100 V/cm. The voltage may be delivered in a variety of waveforms, pulse durations, frequencies, pulse widths, and number of pulses. If a CVDD is used the pulses can be from about 1 V/cm to about 500V/cm, preferably from about 10 V/cm to about 300 V/cm, more preferably about 50 V/cm to about 100 V/cm. In one alternate treatment 50 V/cm is generated by CVDD for 20 msec, at 1 Hz for 1 minute. In another 300 V/cm is generated for 1 msec at 1 Hz for 1 to about 60 seconds.

Figure 7:
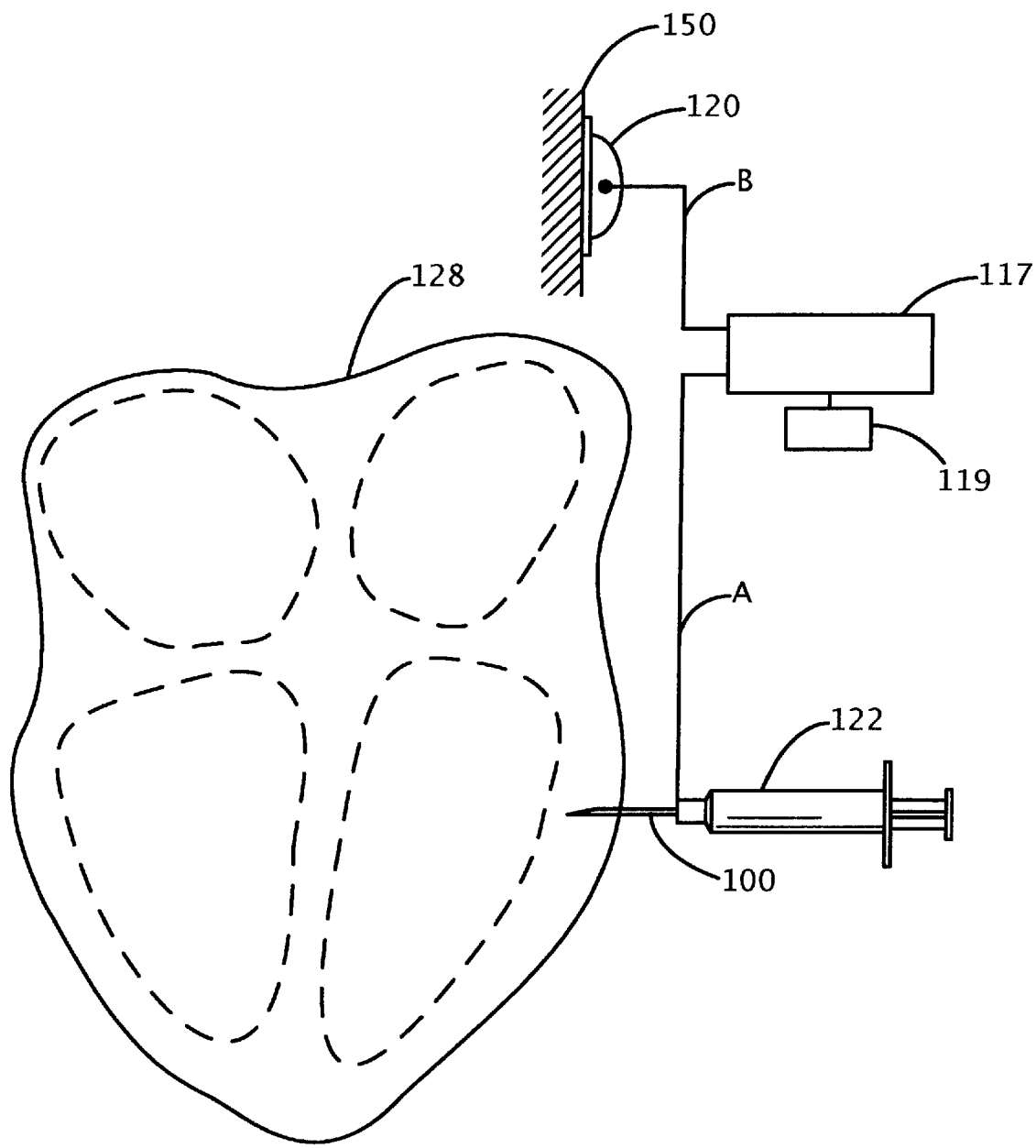
FIG. 7 schematically illustrates another alternative application of the electrical stimulation apparatus shown in FIG. 2.

In another possible application as shown in FIG. 7, the needle 100 can be inserted into the myocardium of the heart 128. In this application, the needle 100 is typically inserted into or proximal to a zone of ischemia. In this application, the location of the patch-type electrode 120 depends on whether the procedure is used with minimally invasive techniques such as an orthoscopic incision, or whether an open heart surgery is performed. If a minimally invasive technique is used, the patch-type electrode is place against the surface of the patient's body 150, such as the abdomen or thigh. If open heart surgery is performed, the patch-type electrode 120 can be placed near or against the surface of the myocardium. Again, the bipolar needle 101 may also be used in this application in place of the needle 100.

In yet another possible embodiment, multiple needles could be inserted into the target area and polarized. These needles could be configured to all have the same polarity. Alternatively, some of the needles have one polarity and the other needles have an opposite polarity to form a bipolar electrode configuration. Such a bipolar configuration may not include the patch-type electrode. One possible embodiment of a multiple needle device is disclosed in United States Patent Application entitled MULTI-LEAD SENSING AND AGENT DELIVERY TO THE MYOCARDIUM, the disclosure of which was incorporated by reference hereinabove.

In yet another possible embodiment (not shown), the needle 100 is mounted on a trans-vascular catheter that can be introduced into a patient's vascular system and threaded to a target area. In one possible procedure, a trans-vascular catheter is used to introduce the needle 100 into one of the chambers of the heart and then to deploy the needle 100 into the myocardium. Such a catheter is described in more detail in U.S. patent application Ser. No. 08/898,656, filed on Jul. 22, 1997 and entitled IONTOPHORETIC DELIVERY OF AN AGENT INTO CARDIAC TISSUE, the disclosure of which is hereby incorporated herein by reference. The bipolar needle 101 also can be used with a trans-vascular catheter.

Figure 8A:
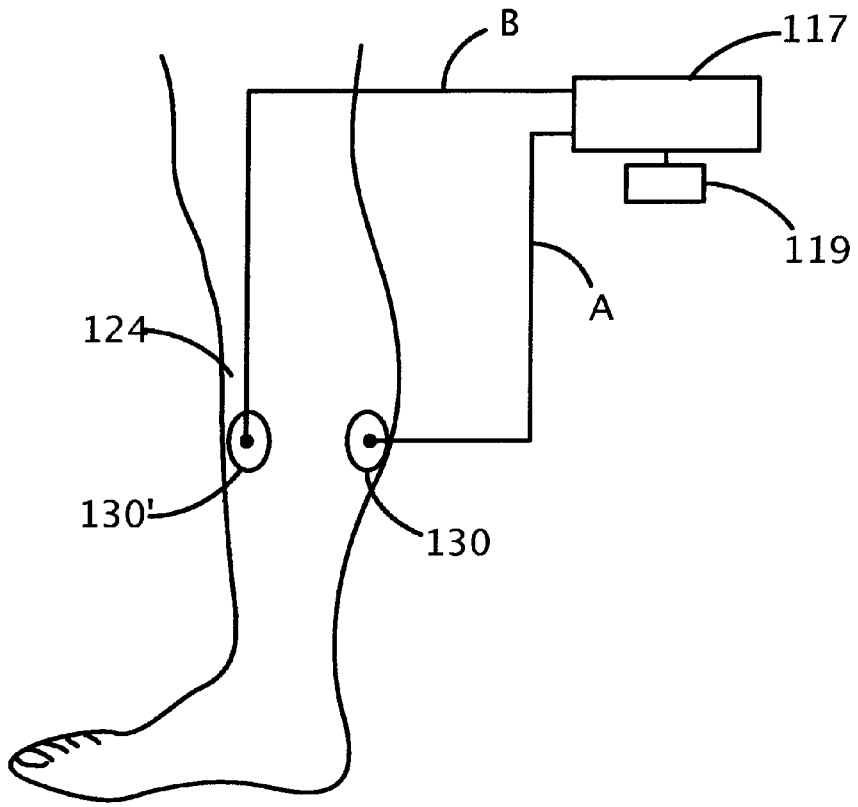
FIG. 8A schematically illustrates an alternative embodiment of an application of an alternate electrical stimulation device having two electrodes, both of which are patch-type electrodes.
Figure 8B:
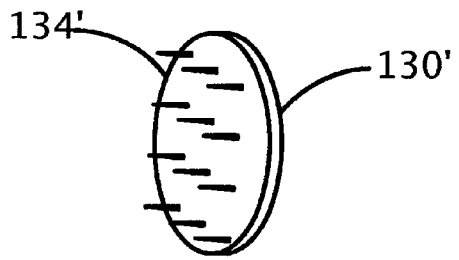
FIG. 8B is a perspective view of the contact surface of the alternate patch-type electrode 130 shown in FIG. 8A having a plurality of pins which can insert into the body tissue.
Figure 8C:
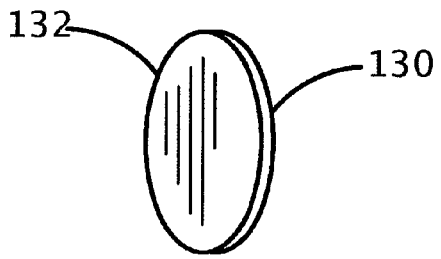
FIG. 8C is a perspective view of an alternate patch-type electrode 142 having a plurality of electrode surfaces 144 which can contact the surface of a targeted body tissue to deliver an electrical current.

Referring now to FIGS. 8A, 8B and 8C, an alternative embodiment of the present invention uses a second patch-type electrode 130 as the primary electrode. The second patch-type electrode 130, which is for application proximal to or over the target area, has a delivery surface 132 configured to be placed against a bodily surface. An advantage of using a patch for the primary electrode 130 is that its size is adjustable, which allows for the entire target area to be incorporated into the electric field. This adjustability also allows the size to be adjusted so that otherwise healthy tissue is not covered by the primary electrode 130, which maximizes the current density in the target tissue.

In one possible configuration of the second patch-type electrode 130', there are a plurality of projecting structures 134' that can penetrate at least the outer surface of the tissue. An example of such a structure is small pin points 134'. These projecting structures have several advantages. One such advantage is that they increase the surface area of the electrode which permits a greater density of the current being radiated from the electrodes. Another advantage is that the outer layer of the skin is more resistive than internal tissue. Thus piercing this outer layer will permit electrical current delivery at lower resistance to the target area. In yet another possible configuration, there are not any projecting structures that pierce the tissue surface. An advantage of not having any piercing structures is that the procedure becomes noninvasive during applications to the outer surface of the patient's body, which is more comfortable for the patient and reduces the risk of infection.

Figure 9A:
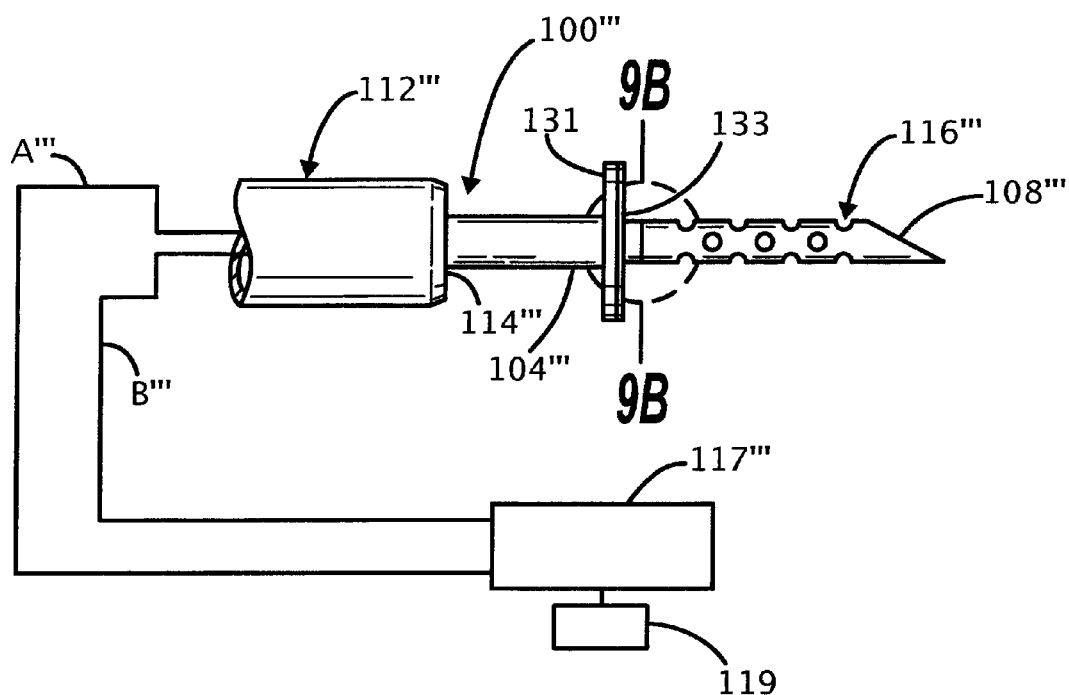
FIGS. 9A–9B schematically illustrate an alternative embodiment of the electrical stimulation apparatus shown in FIGS. 4A and 4B in a similar manner.
Figure 9B:
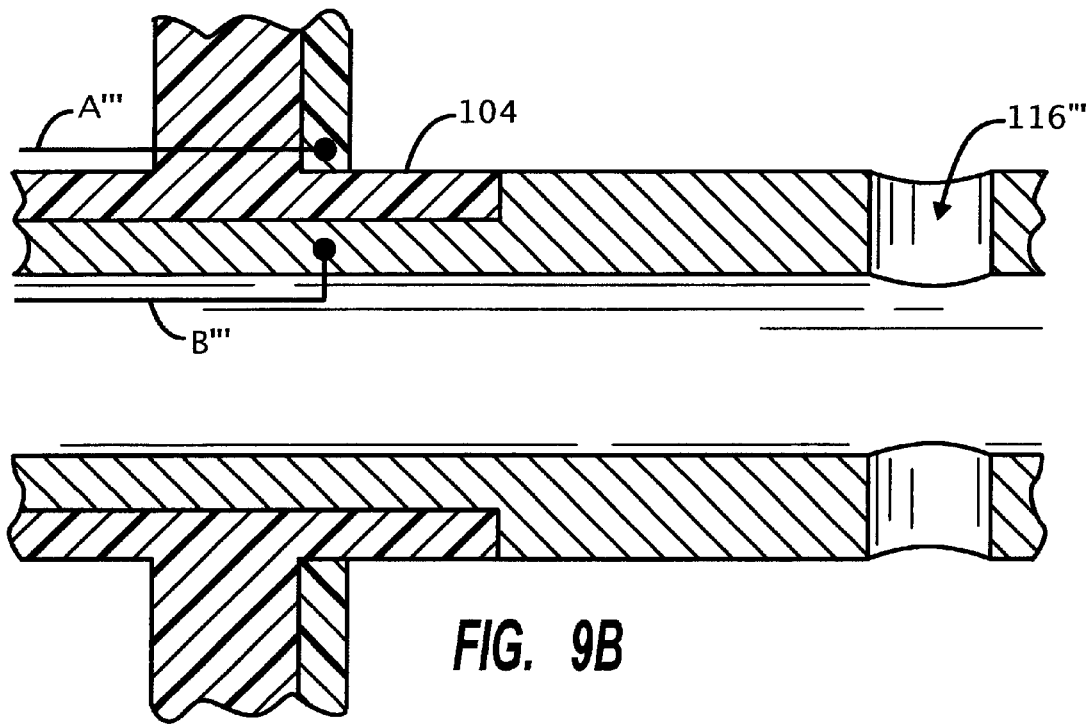

Another possible embodiment of the needle 100''' is shown in FIGS. 9A–9B. In this embodiment, an electrode support member 131 is connected to the needle 100''' adjacent to the insulating material 104 and projects outward therefrom. An electrode 133 is positioned on the electrode support member 131 and faces the tip 108''' of the needle 100'''. In one possible embodiment (not shown), the electrode 133 is spaced apart from the insulating material 104. In another possible embodiment (not shown), the electrode 133 extends over the surface of the electrode support member 131 and is directly adjacent to the insulating material 104'''. In these configurations the insulating material 104''' and the electrode support member 131 insulate the electrode 133 from the needle 100''' and prevents a short circuit. As shown in FIG. 9B, the support member 131 can also be formed as a part of the insulating material 104''' In use, the needle 100''' is inserted into the myocardium until the electrode 133 is in contact with the surface of the myocardium. An advantage of this configuration is that the current conducted between the needle 100''' and the electrode 133 can be controlled to a relatively discrete area.

Figure 10:
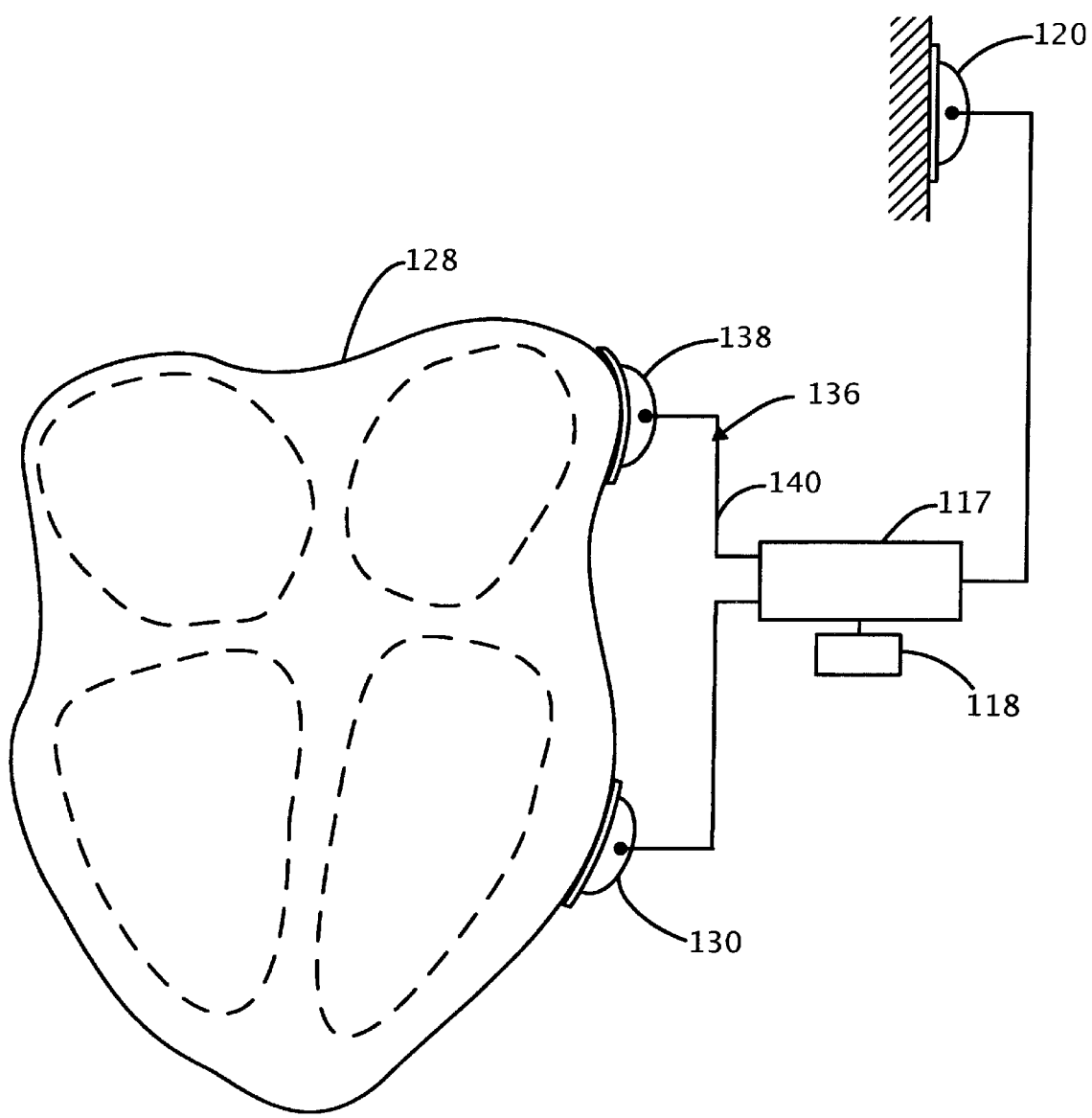
FIG. 10 schematically illustrates an alternate application of a further embodiment of the electrical stimulation apparatus of the present invention.
Figure 11D:
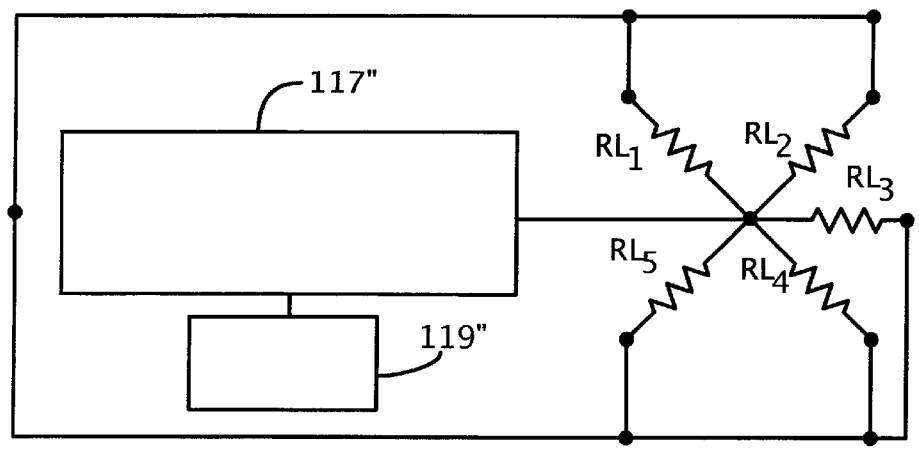

Referring now to FIG. 10, yet another possible embodiment includes a sensing lead 136 that includes a sensing electrode 138 and a lead 140 that is preferably in electrical communication with the source of current 117 and the CPU 118. In use, both the sensing lead 136 and the second patch-type electrode 130 are placed against the myocardium of the heart 128. The sensing lead 136 can be placed into electrical contact with any portion of the heart where a strong signal from the heart's intrinsic electrical activity can be detected. Examples include portions of the myocardium such as the epicardial surface, the myocardium that forms the left or right ventricles, the sinoatrial node, the atrioventricular node and the like.

The sensing lead 136 is then used to sense the electrical impulses in the cardiac conduction system, which causes the heart to beat. In response to sensing these electrical impulses, the circuitry in the source of current 117 and the CPU 118 synchronizes delivery of electrical current with the refactory period of the heart beat, which is the period between depolarization and repolarization of the heart. Synchronization is advantageous because the heart is least susceptible to the inducement of arrhythmia during the refectory period.

In alternative configurations, the circuitry in the source of current 117 and the CPU 118 paces the heart 128 if the heart beat is irregular. Such pacing is accomplished by sending an electric pulse into the heart 128 that causes it to depolarize. The caregiver can then more accurately synchronize the current to the refectory period of the heart. Cardiac pacing is disclosed in U.S. Pat. No. 5,634,899, which was incorporated by reference above.

Yet another alternative embodiment that is useful in cardiac applications does not have any type of synchronizing or pacing circuitry in the source of current 117 and the CPU 118. Choice of electric pulse amplitude, pulse width, pulse frequency, and number of pulses, is tailored to avoid stimulation of arrhythmia. In one possible embodiment, the electrical signal has pulses with a constant voltage amplitude between about 50 V/cm to about 300 V/cm or a constant current amplitude between about 5 mA to about 250 mA, with a frequency between about 0.1 Hz to about 2 Hz. Although various numbers of pulses can be applied in a treatment, one possible treatment is in the range from about 1 pulse to about 60 pulses.

Envisioned in a further alternate embodiment (not shown) is a dedicated electrode system designed specifically for implantation, allowing chronic administration of electric current to target tissue for purposes of stimulating angiogenesis. In principal, any conductor, such as metal or electrically conducting organic polymer (or combination of the two), can serve as the electrode material. Design of the electrode can take on a number of different shapes, and sizes, depending on the nature of the target tissue. In the case of heart muscle or other tissue, the electrode(s) can consist of a straight pin, a screw, a helix, or a patch. The patch can be further divided into mechanisms for delivery either to a smooth surface for contact with the heart, or with various barbs, hooks, needles, clamps, stapels, and the like for penetration into some portion of the heart muscle. Penetrating electrodes could be made hollow, with one or more terminal or side ports, enabling delivery of water, saline, or pharmaceutical agent solutions into or to the surface of target tissue. Drug delivery, however, is not a requisite for electrically mediated angiogenesis. Some advantage might be achieved by use of electrical insulation on some portion of an electrode, which can provide a useful mechanism for directing electric energy in a most desired manner within or to a target tissue.

Similar electrode arrangements are envisioned for other target tissues. In addition, strap type electrodes can be used with applications to target tissues such as bone, where it might be desired to wrap the electrode around the bone or other body tissue.

Electrical leads from the electrodes would be connected to a power source similar to those disclosed herein or commonly used in other implantable battery driven devices. Most convenient would be a source which is implanted into a location which does not interfere with the patient, and can be generally ignored until such time that a battery power source would require replacement.

The electrode systems or needles used with the present invention may be monopolor or bipolar. A mono electrode system has an electrode of one polarity positioned on one structure and an electrode of an opposite polarity positioned on a different structure. In a bipolar electrode, electrodes of both polarities are mounted on a single structure such as a needle, catheter or probe and are electrically isolated from one another. Additionally, a single electrode may be used for each polarity or a group of electrodes might be used. For example, there might be two or more electrodes placed over a diseased area of a limb where it is desired to stimulate the growth of new vasculature. Additionally, the materials used to form the electrodes may be either sacrificial or nonsacrificial. Examples of sacrificial materials include silver/silver chloride, copper, tin, nickel, iron, lithium, and amalgams thereof. Examples of nonsacrificial materials include platinum, gold, and other noble metals. The electrodes also can be formed with zirconium, iridium, titanium, certain carbons, and stainless steel, which may oxidize under certain circumstances. The polarity of the delivering as well as the return electrode may be in either direction as long as the circuit is closed.

The circuits diagrammed in FIGS. 11A–11D are circuits which are representative of a number of applications described herein. In each case the resistance RL is provided by the targeted body tissue. In each case any of the previously described EFGUS 117 can be employed in the respective circuit. Similarly, any appropriate CPU 119 can provide computer processing central for the EFGU 117.

In addition to the in vivo and in vitro method described above, an alternative embodiment can be used with an ex vivo process. In an ex vivo process, cells such as muscle cells, endothelial cells and the like, preferably autologous cells in culture, are treated with electrical current and then injected into an ischemic zone. The process includes providing living cells, preferably autologous living cells which have been removed form the prospective patient, which are biologically compatible with the targeted body tissue; stimulating the living cells with an electrical field sufficient in a manner describe herein to increase VEGF expression by the living cells, wherein the amplitude of the electrical field delivered to the targeted body tissue and the duration of the period of delivery is sufficient to cause the living to increase VEGF expression, and injecting the stimulated cells into the targeted body tissue. This process eliminates the need for in vivo stimulation by electric energy.

As described above, the use of low levels of electrical energy stimulates the target tissue's natural ability to heal or revascularize in an ischemic area. The delivery of electrical current generally improves blood pressure and increases capillary density in both ischemic tissue and in other body tissues as well. It also has been shown to cause upregulation of various cellular materials resulting in increased angiogenesis. In particular, passing low amperage electrical current through body tissues causes cells to increase overall expression of vascular endothelial growth factor (VEGF), which is believed to promote revascularization of body tissues, as well as the expression of the tyrosine kinase receptor (KDR) receptor on endothelial cells, also believed to be important in promoting revascularization in body tissue. This treatment can, under certain conditions, also cause cells to modulate their expression of either acidic or basic fibroblast growth factors (FGFs) which is also believed to promote revascularization or angiogenesis. This enhancement is demonstrated with the following experimental examples.

EXAMPLE 1

In Vitro Cellular VEGF Induced Migration

FIG. 10 illustrates equipment for demonstrating in vitro cellular VEGF induced migration. Cells are grown on a Corning Costar® Transwell System. The transwells are then inserted into the holding chamber containing a conductive media. An electrode is placed in the lower chamber and one in the transwell. The bottom of the transwell is a microporous membrane which allows media and current to pass through while cells remain in the upper (transwell) chamber. This system is advantageous for modeling human systems. It allows for the collection of data that relates to upregulation of such genetic factors as vascular endothelial growth factor (VEGF), known to have an active roll in angiogenesis.

During the experiment the epithelial cells are first grown to confluency in the transwell system and then serum-starved for 24 hours. The cells are then placed into the holding chamber and stimulated with 5 mA DC current for 3 minutes. The negative electrode is placed in the top well containing PBS and the cells. The positive electrode is placed in the lower chamber with M199 low serum media. The cells are then allowed to recover in whole serum for 24 hours. They are then starved again for another 24 hours to mimic ischemic conditions. At the end of this starvation period the cells are trypsinized, counted, and equal amounts of the cells are mounted in a modified Boyden chamber, which is well known in the art. Approximately 20,000 cells are placed into the upper well. VEGF as a chemoattractant is placed in the lower well. After 4 hours of migration the membrane is fixed and stained, and the migration patterns of cells in each condition are evaluated. All conditions are repeated in triplicate.

Western Blot analysis showed an increase in proteins for both the KDR receptor and VEGF with electrical stimulation. The Boyden chamber results indicated that there was an increase in migration, as shown in FIGS. 1A–1C, with current alone verses that with no current. This supports the hypothesis that the electrical stimulation activated the cells.

EXAMPLE 2

Effect of Electric Current Delivery on phVEGF165 Treatment in Rabbit Model

A well established rabbit ischemic hind limb model was studied. Twenty-one rabbits were treated 10 days after surgical intervention to promote ischemia. Control rabbits (n=9) received saline or water injection together with electrical stimulation (Group 1). Six rabbits were treated with a gene plasmid coding for VEGF (500 ug) alone without any electrical stimulation (Group 2). Six additional rabbits received iontophoretic delivery of VEGF (Group 3) VEGF delivered along with electrical stimulation. After 30 days the effect on blood pressure (BP) ratio (ischemic/normal) and angiogenic scores (AS) were evaluated. The angiogenic scores relate to an increase in capillary density. The results (mean±SEM) are shown below in Table 1.

All values were significantly higher at follow-up compared to baseline. No differences between the groups were present. Electric current alone had a remarkably positive effect on blood pressure recovery and angiogenesis in the ischemic limb. Addition of VEGF gene plasmid to treatment with electric current did not further improve angiogenesis. Detectable quantities of VEGF were found in the blood of the animals which received electrical stimulation, whereas this result was not the case for non-electrical controls.

TABLE 1

| Group | BP ratio Baseline | BP ratio Follow up (30 d) | AS Baseline | AS Follow up (30 d) |
| --- | --- | --- | --- | --- |
| 1 | 0.45 ± 0.02 | 0.91 ± 0.03 | 0.54 ± 0.02 | 0.67 ± 0.02 |
| 2 | 0.48 ± 0.02 | 0.94 ± 0.03 | 0.54 ± 0.02 | 0.73 ± 0.01 |
| 3 | 0.48 ± 0.03 | 0.84 ± 0.07 | 0.51 ± 0.02 | 0.74 ± 0.03 |

While the invention has been described in conjunction with a specific embodiments thereof, it is evident that other alternatives, modifications, and variations can be made in view of the foregoing description. For example, features of one of the embodiments or methods described above can be combined with features of any of the other embodiments or methods. Alternatively there can be modifications that are not explicitly taught herein, but still embody the spirit of the inventions described herein. Accordingly, the invention is not limited to these embodiments or the use of elements having specific configurations and shapes as presented herein.

What is claimed is:

1. An electrical stimulation apparatus for delivering an electrical field over a predetermined period of time to a targeted body tissue in order to stimulate a cell-initiated angiogenic response in living cells within the targeted body tissue; the electrical stimulation apparatus comprising:

an electrical field generating unit including a power supply and a control mechanism interconnected with the power supply; and a plurality of electrodes designed to deliver an electrical field to the targeted body tissue; the plurality of electrodes being in electrical communication with the power supply; the control mechanism controlling an amplitude and a duration of a period of delivery of an electrical pulse from the power supply to the respective electrodes and to the targeted body tissue when the plurality of electrodes are in proximity with the targeted body tissue at a plurality of first locations such that an electrical field can be generate between the respective electrodes, wherein the amplitude of the electrical field delivered to the targeted body tissue and the duration of the period of delivery is sufficient to stimulate angiogenesis in the targeted body tissue.

2. The electrical stimulation apparatus of claim 1, wherein the control mechanism includes a computer processing unit in electronic communication with the power supply, the computer being programmed to cause the electrical stimulation apparatus to deliver a predetermined amount of electrical current or voltage over a predetermined period of delivery to the plurality of electrodes such that the electrical stimulation apparatus can deliver such electrical current or voltage to the targeted body tissue when the plurality of electrodes are in contact or proximity with the targeted body tissue.

3. The electrical stimulation apparatus of claim 2, the plurality of electrodes including a sensing electrode, wherein the targeted body tissue is the heart and the sensing electrode monitors contractions of the heart and communicates information regarding the contractions to the computer processing unit so that the computer processing unit can synchronize the period of delivery with a series of refractory periods which follow contractions of the heart, the electrical field being delivered to the heart in a series of pulses programmed to be synchronized with the occurrence of the series of refractory periods.

4. The electrical stimulation apparatus of claim 3, wherein the sensing electrode includes heart pacemaking capabilities which allow it to pace the heart to facilitate the synchronization of the pulsed electrical field generation with the occurrence of the refractory period.

5. The electrical stimulation apparatus of claim 1, wherein the electrical field generating unit is a the constant current delivery device, the electrical field is generated by the constant current delivery device and the amplitude of a current delivered to the targeted body tissue is a generally constant current having an amplitude of from about 0.1 mA to about 250 mA.

6. The electrical stimulation apparatus of claim 1, wherein the electrical field generating unit is a the constant voltage delivery device, the electrical field is generated by the constant voltage delivery device and the amplitude of a voltage delivered to the targeted body tissue is a generally constant voltage of from about 50 V/cm to about 300 V/cm.

7. The electrical stimulation apparatus of claim 1, wherein the electrical field is produced by a number of pulses in the range of from 1 to about 1000 pulses with a frequency between about 0.1 Hz to about 5 Hz.

8. The electrical stimulation apparatus of claim 1, wherein the electrical field is produced for a duration between about 0.0001 seconds to several days.

9. The electrical stimulation apparatus of claim 1, wherein the plurality of electrodes are configured in a manner selected from the group consisting of unipolar, bipolar, and multiple electrode configurations.

10. The electrical stimulation apparatus of claim 1, wherein the apparatus is designed and configured to be implantable.

11. The electrical stimulation apparatus of claim 1, wherein the electrodes are placed on a catheter which can be delivered to targeted body tissue through internal lumens in the post body.

12. An electrical stimulation apparatus for delivering an electrical field over a predetermined period of time to a targeted body tissue in order to stimulate an upregulation of VEGF expression by living cells within the targeted body tissue: the electrical stimulation apparatus comprising:

an electrical field generating unit including a power supply and a control mechanism interconnected with the power supply; and a plurality of electrodes designed to deliver an electrical field to the targeted body tissue; the plurality of electrodes being in electrical communication with the power supply; the control mechanism controlling an amplitude and a duration of a period of delivery of an electrical pulse from the power supply to the respective electrodes and to the targeted body tissue when the plurality of electrodes are in proximity with the targeted body tissue at a plurality of first locations such that an electrical field can be generate between the respective electrodes, wherein the amplitude of the electrical field delivered to the targeted body tissue and the duration of the period of delivery is sufficient to cause living cells in the targeted body tissue to have an increased VEGF expression.

13. The electrical stimulation apparatus of claim 12, wherein the control mechanism includes a computer processing unit in electronic communication with the power supply, the computer being programmed to cause the electrical stimulation apparatus to deliver a predetermined amount of electrical current or voltage over a predetermined period of delivery to the plurality of electrodes such that the electrical stimulation apparatus can deliver such electrical current or voltage to the targeted body tissue when the plurality of electrodes are in contact or proximity with the targeted body tissue.

14. The electrical stimulation apparatus of claim 12, wherein the electric field generating unit is a the constant current delivery device, the electrical field is generated by the constant current delivery device and the amplitude of a current delivered to the targeted body tissue is a generally constant current having an amplitude of from about 0.1 mA to about 250mA.

15. The electrical stimulation apparatus of claim 12, wherein the electric field generating unit is a the constant voltage delivery device, the electrical field is generated by the constant voltage delivery device and the amplitude of a voltage delivered to the targeted body tissue is a generally constant voltage of from about 50 V/cm to about 300 V/cm.

16. The electrical stimulation apparatus of claim 12, wherein the electrical field is produced by a number of pulses in the range of from 1 to about 1000 pulses with a frequency between about 0.1 Hz to about 5 Hz.

17. The electrical stimulation apparatus of claim 12, wherein the electrical field is produced for a duration between about 0.0001 seconds to several days.

18. The electrical stimulation apparatus of claim 12, wherein the plurality of electrodes are configured in a manner selected from the group consisting of unipolar, bipolar, and multiple electrode configurations.

19. The electrical stimulation apparatus of claim 12, wherein the apparatus is designed and configured to be implantable.

20. A method of treatment of targeted body tissues in which increased vascularization is desirable; said method of treatment comprising the step of:
stimulating the targeted body tissue with an electrical field sufficient to stimulate angiogenesis in the targeted body tissue when the targeted body tissue is stimulated over a predetermined period of delivery, wherein the amplitude of the electrical field delivered to the targeted body tissue and the duration of the period of delivery is sufficient to cause living cells in the targeted body tissue to increase VEGF expression.

21. The method of treatment of targeted body tissues of claim 20, wherein said method of treatment further comprises the step of:
providing an electrical stimulation apparatus for delivering an electrical field over a predetermined period of time to a targeted body tissue in order to stimulate an upregulation of VEGF expression by living cells within the targeted body tissue: the electrical stimulation apparatus comprising:
an electrical field generating unit including a power supply and a control mechanism interconnected with the power supply; and
a plurality of electrodes designed to deliver an electrical field to the targeted body tissue; the plurality of electrodes being in electrical communication with the power supply; the control mechanism controlling an amplitude and a duration of a period of delivery of an electrical pulse from the power supply to the respective electrodes and to the targeted body tissue when the plurality of electrodes are in proximity with the targeted body tissue at a plurality of first locations such that an electrical field can be generate between the respective electrodes, wherein the amplitude of the electrical field delivered to the targeted body tissue and the duration of the period of delivery is sufficient to cause living cells in the targeted body tissue to have an increased VEGF expression.

22. The method of treatment of targeted body tissues of claim 21, wherein the electrical field generating unit is a the constant current delivery device, the electrical field is generated by the constant current delivery device and the amplitude of a current delivered to the targeted body tissue is a generally constant current having an amplitude of from about 0.1 mA to about 250 mA.

23. The method of treatment of targeted body tissues of claim 21, wherein the electrical field generating unit is a the constant voltage delivery device, the electrical field is generated by the constant voltage delivery device and the amplitude of a voltage delivered to the targeted body tissue is a generally constant voltage of from about 50 V/cm to about 300 V/cm.

24. The method of treatment of targeted body tissues of claim 21, wherein the electrical field is produced by a number of pulses in the range of from I to about 1000 pulses with a frequency between about 0.1 Hz to about 5 Hz and for a duration between about 0.0001 seconds to several days.

25. A method of treatment of targeted body tissues; said method of treatment comprising the step of:
stimulating the targeted body tissue with an electrical field over a predetermined period of delivery; wherein the electrical current is a generally constant low amperage current of which is sufficient to upregulate living cells within the targeted body tissue so that such cells have an increased expression of VEGF following the step of stimulating.

26. The method of treatment of targeted body tissues of claim 25, wherein said method of treatment further comprises the step of:
providing an electrical stimulation apparatus for delivering a predetermined amount of electrical current over a predetermined period of time to a targeted body tissue in order to stimulate a cell-initiated angiogenic response in living cells within the targeted body tissue:
the electrical stimulation apparatus including:
a source of generally constant low amperage electrical current including a power supply and a control mechanism interconnected with the power supply; and
a plurality of electrodes designed to deliver an electrical current to the targeted body tissue; the plurality of electrodes being in electrical communication with the source of generally constant low amperage electrical current; the control mechanism controlling an amplitude and a duration of a period of delivery of an electrical pulse from the power supply to the respective electrodes and to the targeted body tissue when the plurality of electrodes are in proximity with the targeted body tissue at a plurality of first locations such that an electrical field can be generate between the respective electrodes, wherein the amplitude of the electrical current delivered to the targeted body tissue is from about 0.1 mA to about 250 mA and the duration of the period of delivery is equal to or greater than about 1 ms;

the step of stimulating further including contacting the targeted body tissues with each of the plurality of electrodes in a plurality of first locations.

27. The method of treatment of targeted body tissues of claim 25; said method further including displacing at least one of the plurality of electrodes to a second location with respect to the targeted body tissue which is different from the first location in which the displaced electrode was previously in contact with the targeted body tissue; and repeating the step of stimulating the targeted body tissues.

28. The method of treatment of targeted body tissues of claim 27, said method further including displacing at least one of the plurality of electrodes yet again to a further location with respect to the targeted body tissue which is different than a first or a second location with respect to the targeted body tissue; and repeating the step of stimulating the targeted body tissues.

29. The method of treatment .of targeted body tissues of claim 25, said method further including displacing at least one of the plurality of electrodes a plurality of times to a series of different locations with respect to the targeted body tissue; and repeating the step of stimulating the targeted body tissues each time the step of displacing is repeated.

30. A method of treatment of targeted body tissues in which increased vascularization is desirable; said method of treatment comprising the step of:

providing living cells which are biologically compatible with the targeted body tissue stimulating the living cells with an electrical field sufficient to increase VEGF expression by the living cells, wherein the amplitude of the electrical field delivered to the targeted body tissue and the duration of the period of delivery is sufficient to cause the living to increase VEGF expression; and injecting the stimulated cells into the targeted body tissue.

* * * * *